United States Patent
Feuchtwanger, III

(10) Patent No.: US 11,933,652 B1
(45) Date of Patent: Mar. 19, 2024

(54) FLUSHABLE URINE COLLECTOR WITH VOLUME INDICATOR

(71) Applicant: Joseph B. Feuchtwanger, III, South Setauket, NY (US)

(72) Inventor: Joseph B. Feuchtwanger, III, South Setauket, NY (US)

( * ) Notice: Subject to any disclaimer, the term of this patent is extended or adjusted under 35 U.S.C. 154(b) by 0 days.

(21) Appl. No.: 18/479,383

(22) Filed: Oct. 2, 2023

Related U.S. Application Data

(60) Provisional application No. 63/463,430, filed on May 2, 2023.

(51) Int. Cl.
| | |
|---|---|
| *A61B 5/20* | (2006.01) |
| *A61B 5/00* | (2006.01) |
| *A61B 10/00* | (2006.01) |
| *G01F 19/00* | (2006.01) |

(52) U.S. Cl.
CPC .............. *G01F 19/00* (2013.01); *A61B 5/208* (2013.01); *A61B 5/4381* (2013.01); *A61B 10/007* (2013.01)

(58) Field of Classification Search
CPC ....... G01F 19/00; A61B 5/208; A61B 5/4381; A61B 10/007
See application file for complete search history.

(56) References Cited

U.S. PATENT DOCUMENTS

| | | | | |
|---|---|---|---|---|
| 2010/0243723 A1* | 9/2010 | Partington | .............. | G01F 19/00 229/406 |
| 2010/0314439 A1* | 12/2010 | Partington | .............. | G01F 19/00 220/675 |

OTHER PUBLICATIONS https://www.vernacare.com/products/specimen-collector; Oct. 20, 2022.

* cited by examiner

*Primary Examiner* — Jamel E Williams
(74) *Attorney, Agent, or Firm* — Betsy Kingsbury Dowd, Esq; BKDowd Law, P.C.

(57) ABSTRACT

A urine collector includes a receptacle formed of a water soluble material, which may be a bioplastic, and has a receiving volume for collecting urine therein defined by its shape. The receiving volume is equal to or greater than a predetermined threshold volume. A threshold volume indicator is configured to correspond to the predetermined threshold volume. The urine collector is configured to float in water and to remain buoyant for a time sufficient to allow a user to compare a volume of urine collected in the receiving volume to the threshold volume indicator. The urine collector may be stackable. The water soluble material may be layered on a substrate, which may be a thin sheet of paper, and may further be a non-stick paper product, such as parchment paper.

20 Claims, 6 Drawing Sheets

FLUSHABLE URINE COLLECTOR WITH VOLUME INDICATOR

CROSS-REFERENCE TO RELATED APPLICATIONS

This application claims the benefit of and priority to U.S. Provisional Application Ser. No. 63/463,430 entitled "FLUSHABLE URINE COLLECTOR WITH VOLUME INDICATOR," filed May 2, 2023, the entirety of which is hereby incorporated herein by reference thereto.

FIELD OF DISCLOSURE

The present disclosure relates generally to disposable urine collectors and, in particular, to disposable urine collectors with volume indicators that can be safely flushed after use.

BACKGROUND

Prostate cancer was the second leading cause of cancer death for men in the United States in 2022, according to the National Cancer Institute. This cancer particularly impacts older men, with the risk of men developing prostate cancer increasing from below 1% for those under fifty (50) to a 9 to 10% probability of men over 70 receiving a prostate cancer diagnosis.

Early prostate cancer rarely causes any symptoms. However, if the cancer grows, or if the prostate becomes enlarged for other reasons, the flow of urine is disrupted, and it becomes difficult to empty one's bladder completely. One simple way of self-monitoring for possible prostate cancer or other prostate issues, therefore, is to simply measure the amount of urine passed each time and report this information to one's physician.

Accordingly, there is a need for a urine collector with a volume indicator that can facilitate regular monitoring of the amount of urine passed each time, in order to flag any prostate issues.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure is directed to a urine collector with a volume indicator that can facilitate regular monitoring of the amount of urine passed at one time.

The urine collector includes a receptacle having a bottom wall with a bottom perimeter, a side wall extending upward from the bottom perimeter, an upper perimeter of the side wall, and a receiving volume defined by a shape of the urine collector, wherein the receiving volume equals or exceeds a predetermined threshold volume.

In embodiments, an interior surface of the side wall includes a volume indicator. The volume indicator may be a line etched, embossed, or printed inside the urine collector that corresponds to the predetermined threshold volume. Alternatively, the volume indicator can be a change of color in the material inside the urine collector above and below the predetermined threshold volume.

In further embodiments, a plurality of volume indicators can be provided, one of which corresponds to the predetermined threshold volume, each having the associated enumerated volume printed, etched or embossed next to the volume indicator for a more accurate reading of the volume of urine passed.

In one embodiment, the side wall is tapered between the upper perimeter and the bottom perimeter to form a frusto-conical outer side wall. In preferred embodiments, the side wall tapers inward from the upper perimeter to the bottom perimeter, the upper perimeter having a diameter that is larger than that of the lower perimeter.

In embodiments, the bottom wall is flat.

In other embodiments, the bottom wall has a convex shape, curving convexly downward and inward from the sidewall, such that a center of the bottom wall is the lowest part of the bottom wall.

In another embodiment, the receptacle further includes an inner side wall with an inner perimeter defining an inner edge of the bottom wall, and a central top portion, wherein the bottom wall extends inwardly from the bottom perimeter to the inner perimeter of the inner side wall, such that the bottom wall and inner side wall form an outer annular portion of the receptacle. The inner side wall extends upwardly and inwardly from the inner edge of the bottom wall and terminates at the central top portion.

In embodiments, the shape and dimensions of the bottom wall, the central top portion, the side wall, and the inner side wall are configured to define a subvolume of the receiving volume, wherein the subvolume is equal to the predetermined threshold volume.

In embodiments, the central top portion is flat.

In other embodiments, the central top portion forms a curved apex of a conical surface formed by the inner side wall sloping upwardly and inwardly along a conical surface from the inner perimeter, i.e., from the inner edge of the bottom wall.

The urine collector is, in embodiments, configured to float in water, e.g., in a toilet and to remain buoyant long enough for a user to easily view whether or not the urine output exceeds the predetermined threshold volume, without removing the urine collector from the toilet.

Preferably, the urine collector is formed from a material that is suitable for flushing down a toilet.

In embodiments, the material is biodegradable.

In embodiments, the material is water soluble. Preferably, the material that forms the urine collector is configured to dissolve after the urine is collected and the volume indicator is observed by a user.

In embodiments, the urine collector will begin to dissolve after at least one minute.

In embodiments, the urine collector will dissolve fully within 20 minutes.

In embodiments, the urine collector will dissolve fully within 30 minutes.

In embodiments, the urine collector will dissolve fully within an hour.

In embodiments, the urine collector will dissolve fully within 3 hours.

Various materials are contemplated to form the urine collector, which may include biodegradable materials. In preferable embodiments, the material is water soluble and, preferably, environmentally safe.

The present disclosure is also directed to a urine collector including: a receptacle formed of a water soluble material and having a receiving volume for collecting urine therein defined by its shape, wherein the receiving volume is equal to or greater than a predetermined threshold volume; and a threshold volume indicator configured to correspond to the predetermined threshold volume; wherein the urine collector is configured to float in water and to remain buoyant for a time sufficient to allow a user to compare a volume of urine collected in the receiving volume to the threshold volume indicator.

The threshold volume indicator may be provided by an indicator on an interior surface of the receptacle.

In embodiments, the interior surface may have a first surface color above the predetermined threshold volume that contrasts with a second surface color below the predetermined threshold volume, wherein the threshold volume indicator is a level corresponding to an intersection between the first surface color and the second surface color.

In embodiments, the threshold volume indicator is provided by a subshape of the receptacle, wherein the subshape is configured to define a subvolume of the receiving volume corresponding to the predetermined threshold volume, such that the predetermined threshold volume of urine is collected if the volume of urine collected completely fills or overfills the subvolume.

The urine collector may further include, in embodiments, a lip extending outwardly from an upper perimeter of the receptacle.

In embodiments, the water soluble material of the receptacle is configured to begin to dissolve after one minute.

The water soluble material, in embodiments, is configured to fully dissolve within thirty minutes.

In further embodiments, the water soluble material is configured to fully dissolve within one hour.

The water soluble material, in embodiments, is a bioplastic.

The water soluble material may be a polyhydroxyl polymer, which may be, in embodiments, a polyvinyl alcohol.

In embodiments, the water soluble material includes one or more of polysaccharides, pullulan, starch, and gelatin.

The gelatin may be formed from bovine or porcine materials.

In embodiments, the water soluble material includes Hypromellose.

In other embodiments, the water soluble material includes at least one of polyethylene oxide, polyvinyl pyrrolidone, pectin, rosin, sodium alginate, and chitosan.

The urine collector, in embodiments, may further include a substrate forming an outer surface of the receptacle, wherein the water soluble material is layered on the substrate and forms an interior surface of the receptacle.

In embodiments, the substrate is configured to facilitate separation of the urine collector from a stack of urine collectors.

The substrate may be formed of a non-stick material.

The substrate, in embodiments, may be a thin sheet of water soluble paper.

In other embodiments, the substrate may be formed of parchment paper.

In additional embodiments, the receptacle and the substrate include fold lines configured to fold the urine collector for portability.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the detailed description in conjunction with the accompanying drawings, which are briefly described below.

Figure 1A:
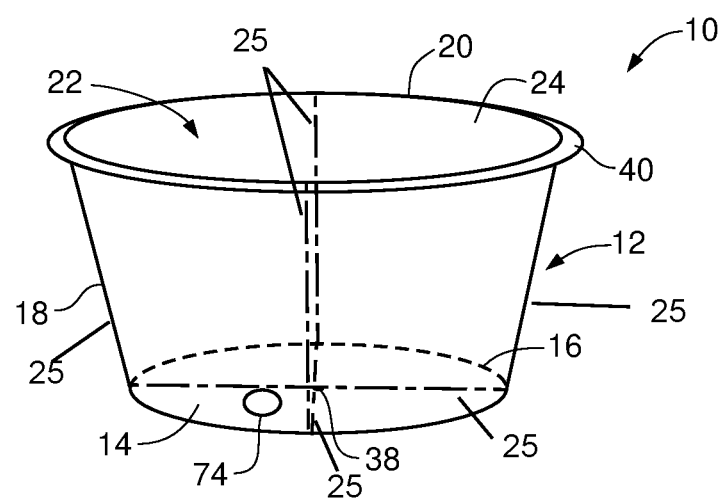
FIG. 1A is a pictorial representation of an embodiment of a urine collector of the present disclosure.

The various aspects of the present disclosure mentioned above are described in further detail with reference to the aforementioned figures and the following detailed description of exemplary embodiments.

DETAILED DESCRIPTION

Particular illustrative embodiments of the present disclosure are described hereinbelow with reference to the accompanying drawings; however, the disclosed embodiments are merely examples of the disclosure, which may be embodied in various forms. It should be apparent to those skilled in the art that the described embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure of a urine collector as defined herein and equivalents thereto. Well-known functions or constructions and repetitive matter are not described in detail to avoid obscuring the present disclosure in unnecessary or redundant detail. Therefore, specific structural and functional details disclosed herein are not to be interpreted as limiting. In this description, as well as in the drawings, like-referenced numbers represent elements which may perform the same, similar, or equivalent functions.

Throughout the description, where items are described as having, including, or comprising one or more specific components or features, or where methods are described as having, including, or comprising one or more specific steps, it is contemplated that, additionally, there are items of the present disclosure that consist essentially of, or consist of, the one or more recited components or features, and that there are methods according to the present disclosure that consist essentially of, or consist of, the one or more recited processing steps.

The present disclosure is directed to a urine collector with a volume indicator that can facilitate regular monitoring of the amount of urine passed at one time.

The term "fully dissolve" as used herein, according to its usual meaning, refers to a structure formed of water soluble material that has broken down completely in water, for example, to the point of the structure no longer being discernible.

Referring to FIG. 1A, an embodiment of a urine collector 10 of the present disclosure includes a receptacle 12 having a bottom wall 14 with a bottom perimeter 16, a side wall 18 extending upward from the bottom perimeter 16, an upper perimeter 20 of the side wall 18, and a receiving volume interior of the side wall 18 and the bottom wall 14 defined by a shape of the receptacle 12, wherein the receiving volume 22 equals or exceeds a predetermined threshold volume.

Figure 1B:
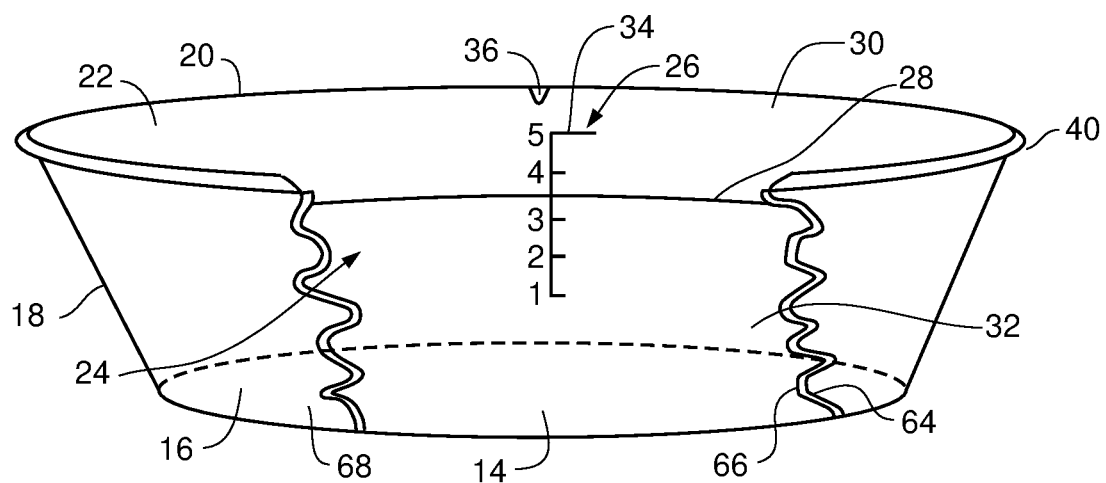
FIG. 1B is a pictorial representation of an embodiment of a urine collector of the present disclosure, such as shown in FIG. 1A, with a cut-away, exposing an embodiment of volume indicators, for example, markings on an inside surface of the urine collector.

In embodiments, referring also to FIG. 1B, an interior surface 24 of the side wall 18 of the receptacle 12 may include one or more volume indicators 26. The volume indicator(s) 26 may be a line etched, embossed, or printed inside the urine collector, for example, on the interior surface 24 of the side wall 18 forming the urine collector 10, that can be used to measure the volume of urine collected in the receptacle 12. One of the volume indicators 26 is a threshold volume indicator 28 that corresponds to the predetermined threshold volume.

In embodiments, the one or more volume indicators 26 is only one volume indicator 26, which is the threshold volume indicator 28 that corresponds to the predetermined threshold volume. The threshold volume indicator 28 may be a line etched, embossed, or printed inside the urine collector 10, for example, on the interior surface 24 of the side wall 18. In the embodiment of FIG. 1B, the predetermined threshold volume is at 3.5 ounces, and is highlighted to the user by extending the threshold volume indicator 28 at the 3.5 ounce mark to be longer than the other volume indicators 26. Preferably, as shown, the threshold volume indicator 28 extends the circumference of the interior surface 24 as a solid line, broken line, an interface between different colors as described below, and so on.

Alternatively, or additionally, the interior surface 24 is constructed with a first surface color 30 above the threshold volume indicator 28 that is different than, and contrasts with, a second surface color 32 below the threshold volume indicator 28. The first surface color indicates a volume above the predetermined threshold volume, and the second surface color indicates a volume below the predetermined threshold volume, so that the threshold volume indicator is, in this embodiment, a level corresponding to an intersection between the first surface color and the second surface color.

In other embodiments, the interior surface 24 above the threshold volume indicator 28, referred to also herein as an upper interior surface, is constructed of a material that changes color upon contact with urine, so that if the volume of urine collected rises above the threshold volume indicator 28, i.e., contacts the upper interior surface, the color change will indicate that the predetermined threshold volume has been met.

Referring to FIG. 1B, in further embodiments, a plurality of volume indicators 26 can be provided, one of which is the threshold volume indicator 28 corresponding to the predetermined threshold volume, for example, as markings or lines 34 on the interior surface 24 of the side wall 18. At least some of the volume indicators 26, in embodiments, has an associated enumerated volume 36 labeled, for example, printed, etched or embossed, in embodiments, next to the corresponding volume indicator 26 for a more accurate reading of the volume of urine passed.

In further reference to FIG. 1B, it should be noted that 3.5 ounces is used as the predetermined threshold volume for exemplary purposes only. It should be clear that the urine collectors of the present disclosure may be configured with any predetermined threshold volume deemed suitable for the particular need. In the example, 3.5 ounces is proposed to represent a reasonable level for urine output in men over fifty, such that if this threshold level is not consistently met, then follow-up care with one's physician to monitor possible prostate issues is indicated.

Referring to FIGS. 1A, 1B, 2A and 2B, in embodiments, the side wall 18 is tapered between the upper perimeter 20 and the bottom perimeter 16 such that the side wall 18 is tapered in a frustoconical shape. In preferred embodiments, the side wall 18 tapers inward from the upper perimeter 20 to the bottom perimeter 16, the upper perimeter 20 having a diameter that is larger than that of the bottom perimeter 16.

In embodiments, the bottom wall 14 is flat.

In other embodiments, the bottom wall 14 is curved. For example, referring to FIG. 1A, the bottom wall 14 may have a convex shape, curving downwardly and inwardly from the side wall 18, such that a center portion 38 of the bottom wall 14 is the lowest part of the bottom wall 14.

Referring still to FIG. 1A, as well as FIG. 1B, any of the embodiments of a urine collector of the present invention may also include a lip 40 extending outwardly from the upper perimeter 20 of the side wall 18 of the receptacle 12.

The lip 40 may be formed of a stiffer material than the receptacle 12.

In other embodiments, the lip 40 may be formed of the same material of the receptacle 12. In particular embodiments, the lip 40 may be thicker than the side wall 18 and or the bottom wall 14.

The lip 40 is preferably configured to enhance the structural integrity of the urine collector, i.e., to maintain the shape of the urine collector 10 long enough to collect the urine and view the volume of urine collected.

Figure 2A:
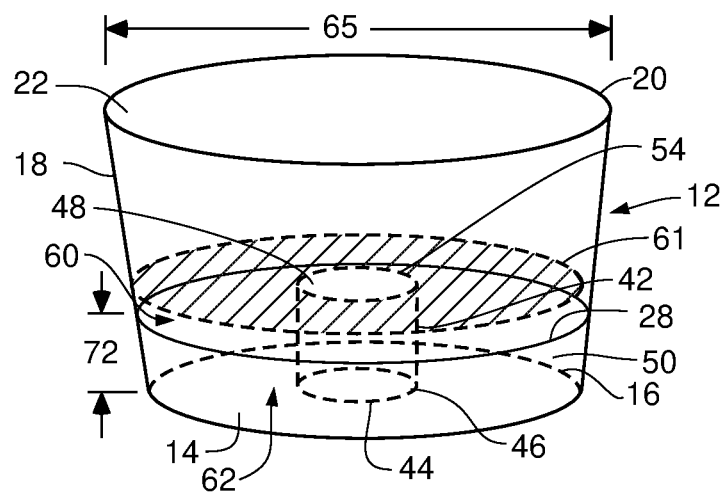
FIG. 2A is a pictorial representation of an embodiment of the urine collector of the present disclosure.
Figure 3:
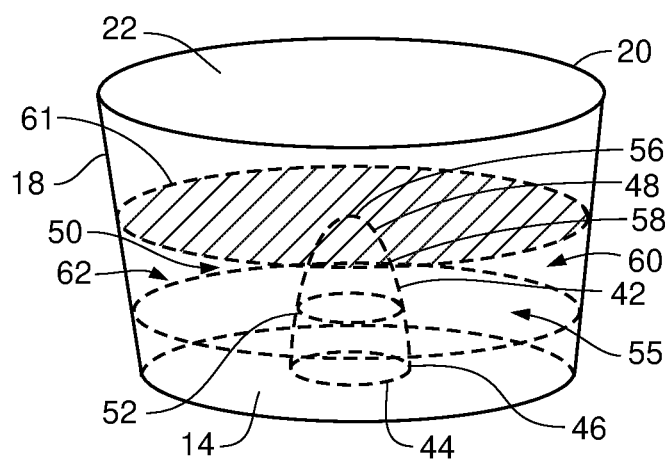
FIG. 3 is a pictorial representation of another embodiment of the urine collector of the present disclosure.

Referring to FIG. 2A, as well as to FIG. 3, in embodiments, the receptacle 12 may further include an inner side wall 42 with a bottom inner perimeter 44 defining an inner edge 46 of the bottom wall 14, and a central top portion 48, wherein the bottom wall 14 extends between the bottom perimeter 16 and the bottom inner perimeter 44 of the inner side wall 42.

Figure 2B:
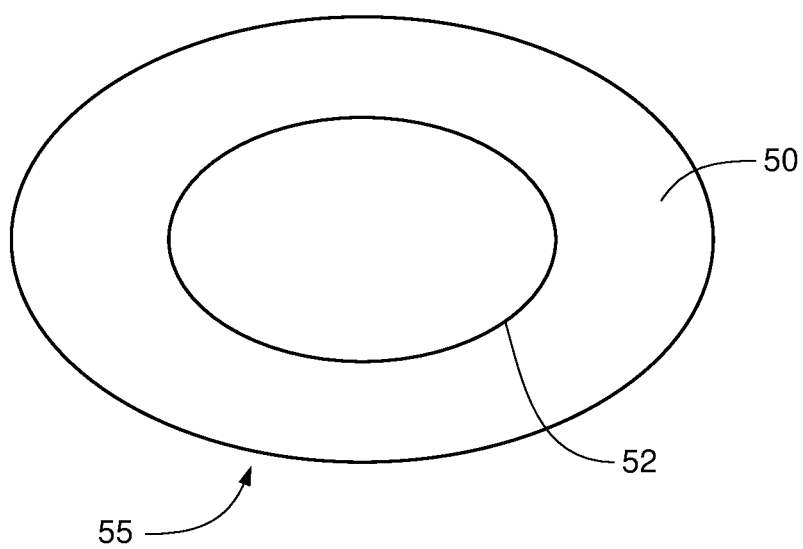
FIG. 2B is a pictorial representation of a transverse slice through an embodiment of a urine collector having an inner side wall.

FIG. 2B represents a transverse slice 55, below the central top portion 48, through an embodiment of the receptacle 12, such as that shown in FIG. 2A, or FIG. 3. As represented by FIG. 2A and FIG. 2B, the cross-sectional shape of the receptacle 12 as defined by the side wall 18, may be circular, or elliptical. In embodiments, the receptacle 12 may include an outer annular portion 50, as described herein, that is further defined between the side wall 18 and the inner side wall 42, which may also have a circular or elliptical shape in cross-sectional plane.

Referring to FIG. 3 and also still to FIG. 2B, in preferred embodiments, the bottom inner perimeter 44, as well as each transverse perimeter 52 of the inner side wall 42 corresponding to each transverse slice 55 of the receptacle 12 below the central top portion 48, may have a circular, or an elliptical shape, such that the inner side wall 42 and the side wall 18 form an outer annular portion 50 of the receptacle 12 below the central top portion 48.

The inner side wall 42 extends upwardly from the inner edge 46 of the bottom wall 14 and terminates at the central top portion 48.

In the embodiment of FIG. 2A, the central top portion 48 is flat. In further embodiments, the central top portion 48 has a top transverse perimeter 54 of the same shape and size as the bottom inner perimeter 44, and of each transverse perimeter 52 below the central top portion 48. In this embodiment, the inner side wall 42 and central top portion 48 form a hollow cylinder with an opening centered in the bottom wall 14.

In a further embodiment shown in FIG. 3, the inner side wall 42 extends upwardly and inwardly from the inner edge 46 of the bottom wall 14 and terminates at the central top portion 48, which, in embodiments, may be flat.

In other embodiments, referring to FIG. 3, the central top portion 48 forms a curved apex 56 of a conical surface 58 formed by the inner side wall 42 sloping upwardly and inwardly from the bottom inner perimeter 44, i.e., from the inner edge 46 of the bottom wall 14.

In embodiments, referring to FIG. 2A, for example, the shape and dimensions of the bottom wall 14, the central top portion 48, the side wall 18, and the inner side wall 42 are configured to define a subvolume 60 of the receiving volume 22. In embodiments, the subvolume 60 may be configured to be equal to the predetermined threshold volume.

Referring to FIGS. 2A and 3, for example, the subvolume 60 corresponds to a volume of fluid, e.g., urine, that fills a subshape 62 of the urine collector. In these embodiments, the subshape 62 is defined by the outer annular portion 50 in FIG. 2A, or by the subvolume 60 below the curved apex 56, underneath an upper border 61 indicated by hatching. In embodiments, if the volume of urine collected exceeds the subvolume 60 defined by the subshape 62, e.g., in embodiments, by the subshape 62, in embodiments outer annular portion 50, having the upper border 61 that is coplanar with the central top portion 48, the central top portion 48 will be covered. Accordingly, in embodiments in which the subshape 62 is configured to correspond to a subvolume 60 that equals the predetermined threshold volume, if the urine collected covers the central top portion 48, then the predetermined threshold volume has been exceeded. This should be quickly and easily viewable by the user.

In other embodiments, the subvolume 60 corresponding to the subshape 62 exceeds the predetermined threshold volume. In these embodiments, the urine collector includes the threshold volume indicator 28 on the interior surface 24, which will be at a level below the central top portion 48. Accordingly, a depth 72 corresponding to the predetermined threshold volume is measured within the subvolume 60 of the receiving volume 22 of the receptacle 12. This depth 72 is greater than a depth that would correspond to the urine collector without the partitioned subvolume 60. This configuration has the advantage of configuring the urine collector with a receiving diameter 65 than would be possible without the subvolume 60, ensuring that all urine passed is collected, while increasing the depth 72 at which the threshold volume indicator 28 is located.

Referring also to FIG. 1B, embodiments of the receptacle 12 of a urine collector of the present disclosure including any embodiment of the subshape 62, including those embodiments represented by FIGS. 2A, 2B and 3, may still additionally have markings or lines as volume indicators 26, on the interior surface 24 of the side wall 18. In embodiments, at least one or more of the volume indicators 26 has the associated enumerated volume 36 labeled, e.g., printed, etched or embossed, next to the corresponding volume indicator 26 for a more accurate reading of the volume of urine collected.

Figure 1C:
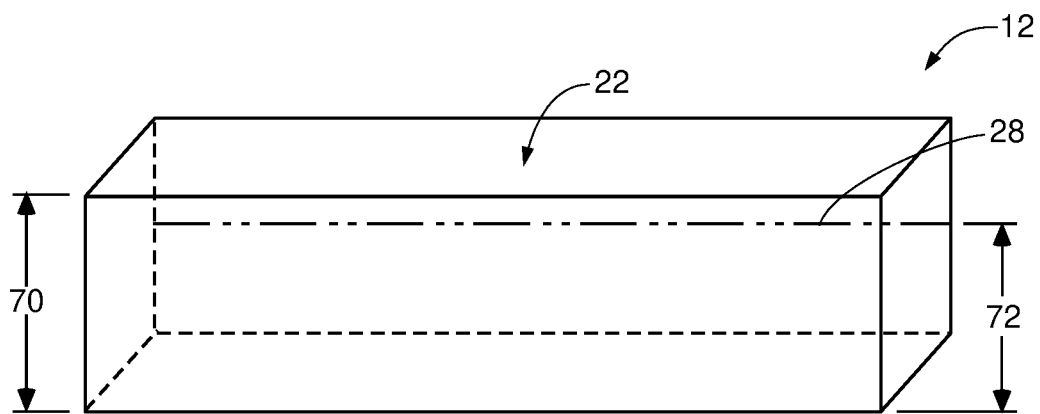
FIG. 1C is a pictorial representation of another embodiment of a urine collector of the present disclosure.

It should be clear to one of ordinary skill in the art that the shape and subshapes of the various embodiments described herein do not have to be of circular or elliptical cross-section, but could alternatively be, but are not limited to, the side wall 18 of the receptacle 12 being rectangular, as shown in FIG. 1C, for example, and in embodiments, including an outer annular portion 50 which is also rectangular-shaped.

Referring to FIG. 1C, once the preferred outer dimensions of the side wall 18 are determined, a depth 70 is determined, such that the receiving volume 22 of the receptacle 12 is configured to hold an amount of fluid, e.g., urine, equal to or greater than a predetermined threshold volume. In embodiments, the receptacle 12 includes a threshold volume indicator 28, as described herein, corresponding to the predetermined threshold volume, and the depth 70 of the receptacle is greater than a depth 72 corresponding to the threshold volume indicator 28.

In embodiments, the depth 70 of the receptacle 12 is 1.5 to 2 times greater than the depth 72 corresponding to the threshold volume indicator 18.

In other embodiments, the depth 70 of the receptacle 12 is more than 2 times greater than the depth 72 corresponding to the threshold volume indicator 18.

It should be appreciated that the outer dimensions of the receptacle 12 cannot be so large that the predetermined threshold volume cannot be easily measured. For example, if the predetermined threshold volume corresponds to only 3.5 ounces, or 103.5 cc, and the receptacle 12 is configured as a cylinder with a cross-sectional diameter of about 10 cm, the depth 72 corresponding to a volume of 3.5 ounces is only about 1.32 cm or a little over ½ inch.

In embodiments, the urine collector may be configured with dimensions of greater cross-sectional area to extend over a larger extent, e.g., covering at least 40%, or preferably at least 60% of a receiving portion of a toilet to ensure collection of all urine passed at one time. In these embodiments, the depth 72 corresponding to the predetermined threshold volume can be configured to correspond to a reasonable, legible, height, by configuring the receptacle 12 to incorporate sub-shapes, as described herein, such that the depth 72 is measured within a subvolume of the receiving volume 22 of the receptacle 12, as shown, for example in FIG. 2A. These embodiments allow for a greater cross-sectional receiving area than would be obtainable with simple shapes shown by FIGS. 1A-1C.

The urine collector of the present invention is preferably shaped and configured to float in water, i.e., in a toilet, and to remain buoyant for a time sufficient to allow a user to easily view whether or not the urine output exceeds the predetermined threshold volume, without removing the urine collector from the toilet. The urine collector is configured to be disposable, for single use, and is preferably safely flushable once the level of urine output has been noted by a user.

In embodiments, referring to FIG. 1A, for example, for additional ease of use, the urine collector may, in embodiments, be configured to be collapsible or foldable, e.g., along one or two fold lines 25 provided on the bottom wall 14 and along opposite portions of side wall 18, such that the fold lines 25 on the side wall 18 intersect with the one or two fold lines 25 on the bottom wall 14. The urine collector 10 in a folded position, folded along fold lines 25, is configured for portability, i.e., to be carried on one's person for later use.

In embodiments described further herein, the urine collector 10 having fold lines 25 for carrying on one's person may also include a substrate 64, for example, a thin sheet of paper or other suitable material, including the same fold lines 25 of FIG. 1A.

As described in reference to the exemplary embodiments of the disclosure, the urine collector may include conventional volume indicators, such as level lines with the corresponding volume marked next to the level lines. However, to simplify and speed up the process of determining whether a sufficient amount of urine is output in a single pass, an easily viewable threshold volume indicator 28, that is distinguishable from the plurality of volume indicators 26, is preferably included. In embodiments, the urine collector includes only one volume indicator 26, which is the threshold volume indicator 28 that corresponds to the predetermined threshold volume. If the urine collected is above the threshold volume indicator 28, this is a good sign that the prostate is healthy. However, if the urine collected in a single instance is below the threshold volume indicator 28, a user can easily determine that the urine output is low, i.e., below, the predetermined threshold volume that could indicate a problem with the prostrate.

Because the urine collector is disposable, and preferably flushable, the user simply flushes the urine collector after use, preferably after logging the day, time, and either a volume of urine passed, in embodiments, by reading the level indicated corresponding to one of a plurality of volume indicators, or simply recording whether or not the output is above the volume indicator that corresponds to the predetermined threshold volume. This information may then be passed on to the user's physician for further follow-up, if needed.

In embodiments, the disposable urine collector is formed of a material that is biodegradable.

In preferred embodiments, the urine collector is formed of a material that is water soluble and safely flushable, and is preferably environmentally safe and non-toxic.

The material must, in embodiments, be configurable to substantially maintain its shape and to remain buoyant long enough to collect the urine passed and allow the user to record the amount of urine collected, in embodiments, for at least a minute, and in further embodiments, for a period of about a minute.

Preferably, the material of the urine collector is configured to completely dissolve within twenty (20) minutes.

In other embodiments, the urine collector formed is configured to completely dissolve within thirty (30) minutes.

In further embodiments, the urine collector formed is configured to completely dissolve within one (1) hour.

In still further embodiments, the urine collector is configured to completely dissolve within three (3) hours.

Various materials are contemplated as being suitable to form the urine collector of the present invention.

In embodiments, the material includes a bioplastic. In further embodiments, the bioplastic is water soluble.

In still further embodiments, the bioplastic material is a polyhydroxy polymer, such as a polyvinyl alcohol.

In embodiments, the material used to form the urine collector may be formed into a suitable shape for collecting urine, including, but not limited to, any one of the shapes of the present disclosure, using molds, or, in other embodiments, by forming seams at the interfaces of the bottom wall and the side wall, and, in embodiments, between the bottom wall, inner side wall and central top portion. The seams may be formed by any appropriate method known in the art, for example, but not limited to heat pressing.

In additional embodiments, the bioplastic material is a composite of polyvinyl alcohol.

In embodiments, the material is any suitable bioplastic capable of forming into a suitable structure for retaining fluid, which may, in embodiments, be formed by dipping a mold in the shape of the receptacle into a solution of a liquid biopolymer, or gelatine, or other materials described herein, extracting it and allowing it to dry, and then removing the material now configured in the shape of the receptacle, drying, and further shaping as necessary.

In embodiments, the material may include a water-soluble film-forming polymer. Polymer film bases with a higher molecular weight will take longer to dissolve, allowing for a polymer-based material to be adjusted to dissolve within a reasonable period of time that is suitable for the urine collector.

Suitable polymers may be used alone or in a composition with other polymers or materials. The material may include one or more polymers, such as polysaccharides, for example, gum polysaccharides and/or pullulan, gelatin, including gelatins formed from bovine or porcine materials, and starch.

Certain types of cellulose may also be appropriate, and like many other polymers, can advantageously add additional structure to a water-soluble material. The material of the urine collector may also, or alternatively, include a cellulose such as hydroxypropyl methylcellulose, also known as Hypromellose.

Additional polymers that may be suitable either alone or in composition with other materials for forming the urine collector include polyethylene oxide, polyvinyl pyrrolidone, pectin, rosin, sodium alginate, and chitosan.

The material may also include, in embodiments, one or more plasticizers to enable shaping the urine collector.

Referring again to FIG. 1B, in further embodiments, the urine collector of the present invention is configured to be stackable.

In still further embodiments, the receptacle 12 is a layered structure which includes a substrate 64 and a layer 66, wherein the layer 66 is formed of any one or more of the materials described above and is preferably water soluble as described supra, layered on the substrate 64.

In preferred embodiments, the layer 66 of preferably water soluble material is layered on top of the substrate 64, so that the layer 66 forms the interior surface 24 of the receptacle 12 and the substrate 64 forms an outer surface 68, as represented in FIG. 1B.

In embodiments, the substrate 64 is a thin sheet of paper, which includes cellulose, and which may have a similar composition as toilet paper, or tissue paper. The substrate 64 is flushable and, in embodiments, may be dissolvable in less time than the thin film 66.

The substrate 64 may be formed of a substrate material that facilitates separating one urine collector from a stack of urine collectors, for example, a non-stick material.

In embodiments, the urine collector is placed in the toilet for use with the layered structure of the layer 66 on the substrate 64 intact, both materials being flushed down the toilet after the user observes the amount of urine collected. By forming the layer 66 on top of the substrate 64 so that the layer 66 of water soluble material forms the interior surface, the time it takes for the substrate 64 to dissolve or to break up and separate from the layer 66, which may be less time than it takes for the material forming the layer 66 to dissolve, will not affect the readability of the threshold volume indicator 28 and/or volume indicators 26.

In other embodiments, the substrate material of the substrate 64 may be a non-stick, hydrophobic material, such as parchment paper. In embodiments, the substrate 64 does not form part of the urine collector as used, but is configured to be separable from the urine collector once it is removed from a stack of urine collectors, and may be disposed of separately, not flushed down the toilet with the urine collector.

In additional embodiments, referring, for example, to FIG. 1A, any of the embodiments of the urine collector may additionally include a test strip or patch 74, located preferably on the interior surface 24 of the bottom wall 14, is configured to detect a medical condition, or an infection, such as a urinary tract infection. In one embodiment, the test strip or patch 74 is configured to turn a predetermined color if a urinary tract infection (UTI) is detected.

Although the urine collector of the present disclosure is especially useful for men to use as an indicator of prostate health, it is certainly not limited to use by men. The urine collector can also use be used by women to collect a predetermined threshold volume of urine, and also for use by women with the patch 74 configured for UTI detection. The patch 74 may be configured for useful detection of conditions, infections, or of any number of components that can be present in urine, for men or women, preferably wherein the patch 74 is configured to change color if a particular condition, infection, or component is present in the urine. Other possible uses of the patch 74 may include, but are not limited to, the detection of ketone levels, glucose levels, and for women, of human chorionic gonadotropin (HCG) and luteinizing hormone (LH) levels.

While particular embodiments of the present disclosure have been particularly shown and described with reference to specific embodiments, it should be apparent to those skilled in the art that the foregoing is illustrative only and not limiting, having been presented by way of example only. It is to be understood that the disclosed embodiments are merely examples of the disclosure, which may be embodied in various forms and detail without departing from the spirit and scope of the disclosure. Therefore, specific structural and functional details disclosed herein are not to be interpreted as limiting. Numerous other embodiments may fall within the scope of the accompanying claims and equivalents thereto.

What is claimed is:

1. A urine collector comprising
  a receptacle formed of a water soluble material and having a receiving volume for collecting urine therein defined by its shape, wherein the receiving volume is equal to or greater than a predetermined threshold volume; and
  a threshold volume indicator configured to correspond to the predetermined threshold volume;
  wherein the urine collector is configured to float in water and to remain buoyant for a time sufficient to allow a user to compare a volume of urine collected in the receiving volume to the threshold volume indicator.

2. The urine collector of claim 1, wherein the threshold volume indicator is provided by an indicator on an interior surface of the receptacle.

3. The urine collector of claim 2, wherein the interior surface has a first surface color above the predetermined threshold volume that contrasts with a second surface color below the predetermined threshold volume, wherein the threshold volume indicator is a level corresponding to an intersection between the first surface color and the second surface color.

4. The urine collector of claim 1, wherein the threshold volume indicator is provided by a subshape of the receptacle, wherein the subshape is configured to define a subvolume of the receiving volume corresponding to the predetermined threshold volume, such that the predetermined threshold volume of urine is collected if the volume of urine collected completely fills or overfills the subvolume.

5. The urine collector of claim 1, further comprising a lip extending outwardly from an upper perimeter of the receptacle.

6. The urine collector of claim 1, wherein the water soluble material is configured to begin to dissolve after one minute.

7. The urine collector of claim 1, wherein the water soluble material is configured to fully dissolve within thirty minutes.

8. The urine collector of claim 1, wherein the water soluble material is configured to fully dissolve within one hour.

9. The urine collector of claim 1, wherein the water soluble material is a bioplastic.

10. The urine collector of claim 1, wherein the water soluble material is a polyhydroxyl polymer.

11. The urine collector of claim 10, wherein the polyhydroxyl polymer includes a polyvinyl alcohol.

12. The urine collector of claim 1, wherein the water soluble material includes one or more of polysaccharides, pullulan, starch, and gelatin.

13. The urine collector of claim 12, wherein the gelatin is formed from bovine or porcine materials.

14. The urine collector of claim 1, wherein the water soluble material includes Hypromellose.

15. The urine collector of claim 1, wherein the water soluble material includes at least one of polyethylene oxide, polyvinyl pyrrolidone, pectin, rosin, sodium alginate, and chitosan.

16. The urine collector of claim 1, further comprising a substrate forming an outer surface of the receptacle, wherein the water soluble material is layered on the substrate and forms an interior surface of the receptacle, wherein the substrate is configured to facilitate separation of the urine collector from a stack of urine collectors.

17. The urine collector of claim 16, wherein the substrate is formed of a non-stick material.

18. The urine collector of claim 16, wherein the substrate is a thin sheet of water soluble paper.

19. The urine collector of claim 17, wherein the substrate is formed of parchment paper.

20. The urine collector of claim 16, wherein the receptacle and the substrate include fold lines configured to fold the urine collector for portability.

* * * * *